(12) United States Patent
Colombo et al.

(10) Patent No.: US 7,951,401 B2
(45) Date of Patent: May 31, 2011

(54) STABILISED SOLID DRUG DISPERSIONS IN AN ORGANIC CARRIER AND A PROCESS FOR PREPARING THE SAME

(75) Inventors: Italo Colombo, Inzago (IT); Dario Gervasoni, Carugate (IT)

(73) Assignee: Eurand S.p.A., Pessano Con Bornago (IT)

( * ) Notice: Subject to any disclaimer, the term of this patent is extended or adjusted under 35 U.S.C. 154(b) by 1125 days.

(21) Appl. No.: 10/540,139

(22) PCT Filed: Dec. 22, 2003

(86) PCT No.: PCT/EP03/14740
§ 371 (c)(1),
(2), (4) Date: Jun. 21, 2005

(87) PCT Pub. No.: WO2004/056340
PCT Pub. Date: Jul. 8, 2004

(65) Prior Publication Data
US 2006/0051422 A1 Mar. 9, 2006

(30) Foreign Application Priority Data

Dec. 23, 2002 (IT) .............................. MI2002A2748

(51) Int. Cl.
*A61K 47/30* (2006.01)
*A61K 9/14* (2006.01)
(52) U.S. Cl. ....... 424/489; 424/46; 424/486; 514/772.3; 514/772.7; 514/788.1
(58) Field of Classification Search ................... None
See application file for complete search history.

(56) References Cited

U.S. PATENT DOCUMENTS

| 5,447,077 A | * | 9/1995 | Lautenschlager | .......... 73/863.11 |
| 5,972,381 A | | 10/1999 | Sangekar et al. | |
| 6,123,936 A | * | 9/2000 | Platz et al. | .................. 424/85.6 |
| 6,462,093 B1 | * | 10/2002 | Miyamoto et al. | ......... 514/772.3 |

FOREIGN PATENT DOCUMENTS

| EP | 1 308 156 | * | 5/2003 |
| EP | 1308156 | | 5/2003 |
| JP | 5306225 | | 11/1993 |
| WO | WO 97/06781 | * | 2/1997 |
| WO | 98/00113 | | 1/1998 |

OTHER PUBLICATIONS

Burgese et al. "microwave Generated Nanocomposites for Making Insoluble Drugs Soluble", Materials Science and Engineering: C vol. 23, Issues 6-8, available online Oct. 27, 2003.*
website: http://whatis.techtarget.com—def'n of dielectric material, (dated Aug. 12, 2008).*
website: www/milestonesci.com; Microwave Synthesis—Technical Details for Ethos MicroSYNTH multimode microwave applicator, (dated Aug. 12, 2008).*
website: Answers.com for Standard Temperature and Pressure definition for std. pressure in units of bar, (dated Aug. 12, 2008).*
Hawley's Condensed Chemical Dictionary (13th Ed.); p. 68 for the definition of "amorphous", (pub'd 1997).*

* cited by examiner

*Primary Examiner* — Robert A Wax
*Assistant Examiner* — Jeffrey T Palenik
(74) *Attorney, Agent, or Firm* — Christensen O'Connor Johnson Kindness PLLC

(57) ABSTRACT

New solid drug dispersions are described in which a drug is present in amorphous form and dispersed within the particles of an organic carrier selected from cross-linked polymers and/or complexing agents. These dispersions are obtainable by mixing the drug and the carrier and applying an oscillating electromagnetic field in the microwave region according to a specific heating cycle wherein the drug-carrier mixture is heated at a temperature higher than the melting point of the drug for at least 5 minutes.

11 Claims, 6 Drawing Sheets

STABILISED SOLID DRUG DISPERSIONS IN AN ORGANIC CARRIER AND A PROCESS FOR PREPARING THE SAME

FIELD OF THE INVENTION

The present invention refers to the field of rapid effect pharmaceutical compositions provided with high bioavailability. The preparation of new drug-carrier composites (stabilised solid dispersions) is described in which the drug is massively dispersed (in bulk) in amorphous form inside an organic carrier.

PRIOR ART

The attainment of ready to use pharmaceutical compositions, which ensure high solubilisation kinetics of the drug and therefore a high bioavailability immediately following administration, is an important objective in pharmaceutical technology; such a need is particularly felt in the case of drugs sparingly soluble in water, which notoriously have a low bioavailability.

Many drugs poorly soluble in water are present in the crystalline state: a system to improve the solubility of this group of drugs is that of destructuring the crystalline network, rendering them amorphous: in fact a substance in the amorphous state has both greater solubility and faster dissolution kinetics in water with respect to the corresponding crystalline state. The reason for which lies in the fact that whilst the dissolution of a crystal requires an additional intervention on the part of the solvent to break the intermolecular bonds in the crystalline network, such an intervention is not required in the case of the amorphous form: in the latter case the dissolution procedure requires less energy and the dissolution takes place more rapidly.

The amorphisation procedures for crystalline drugs have been known for a long time (Yu L., *Amorphous pharmaceutical solids: preparation characterisation and stabilization. Adv. Drug. Delivery Rev.,* 2001, 48, p. 27-42). However, due to the greater stability of crystals, (a physical form with lower free energy and, therefore, thermodynamically more stable) the amorphised drugs have poor stability (metastable phase) and tend to easily recrystallise, thus losing their temporarily acquired increased solubility.

With the aim of limiting this phenomenon, it has been proposed to make the amorphous drug deposit on the pharmaceutical carriers: in this case, the drug-carrier interactive forces limit the tendency of the amorphous phase molecule to re-aggregate, which allows them to have a greater stability. To obtain that, "solvent deposition" procedures have been proposed, according to which the drugs are initially dissolved in an appropriate solvent; to this solution are added insoluble carrier particles, and then the solvent is evaporated, thus making the drug in amorphous form precipitate on the carrier.

These strategies however are only partially effective, in that they lead to not very high percentages of amorphisation; in addition, the drug remains deposited only on the external surface of the carrier particles i.e. not distributed internally (in bulk) inside the particles themselves (*International Journal of Pharmaceutics,* 33, 1986, p. 115-124): the drug lying on the surface still shows a notable freedom for re-aggregation easily forming crystalline structures. Recently, some authors (*Drug Dev. Ind. Pharm.,* 24 (4), 1998, p. 359-363) have proposed the use of microwaves to increase the solubility of crystalline drugs: the process provides the mixing of drug with an inorganic carrier with a high surface area (silicon dioxide), and exposure to microwaves; however, even in this case composites are obtained, denominated by the authors "surface solid dispersions", in which the amorphised drug is localised on the surface of the carrier particles. Even in this case the limitations of the previous systems are present, i.e. the drug is deposited only on the external surfaces of the carrier particles, and is therefore still subject to the phenomenon of re-crystallisation.

EP-A-1308156 describes the preparation of solid dispersions of a drug in water-soluble polymers, such as linear polyvinylpyrrolidone, the dispersion being obtained by microwave treatment. U.S. Pat. No. 6,462,093 describes the microwave-assisted preparation of drug-carrier composites; the examples show the use, as carriers, of hydroxypropylmethylcellulose, its acetosuccinate derivative, and linear polyvinylpyrrolidone. In both these references the microwave power (Watt) is kept constant throughout the entire treatment.

Until present, none of the available amorphisation processes is entirely satisfactory. Aim of the present invention is to provide a highly effective process capable to obtain both a high dispersion of the active principle throughout the carrier and also a high degree of amorphisation of the active principle.

SUMMARY

It has now been surprisingly found that when a drug is mixed with an organic carrier and then treated with an oscillating electromagnetic field at frequencies belonging to the microwave region according to a specific heating cycle, a drug-carrier composite is obtained in which the drug is amorphised in higher quantities and in more stable form, with respect to these obtained by the prior art.

In the present invention the treatment with microwaves is carried out on homogeneous mixtures of drug and carrier pre-wetted with appropriate quantities of solvents, or on drug-carrier mixtures in the dry state, placed on dielectric material based supports which couple with the microwaves, such as for example polytetrafluoroethylene loaded with graphite.

The microwave application cycle is such that the drug mixture is heated to a temperature higher than the melting temperature of the drug, and such temperature is subsequently maintained constant for at least 5 minutes. The composites obtained according to the present invention, herein identified as "stabilised solid dispersions", are characterised by containing a quantity of amorphised drug greater than 50% by weight with respect to the total drug present, and by the fact that the drug is also dispersed inside (in-bulk) of the carrier particles, hence not just on the external surface of the same.

The present dispersion technique in-bulk of the drug in amorphous form is seen as being particularly effective and useful in the case of drugs poorly soluble in water, thus allowing the increase in the characteristics of solubility and bioavailability in rapid times following administration.

DETAILED DESCRIPTION OF THE INVENTION

Figure 1:
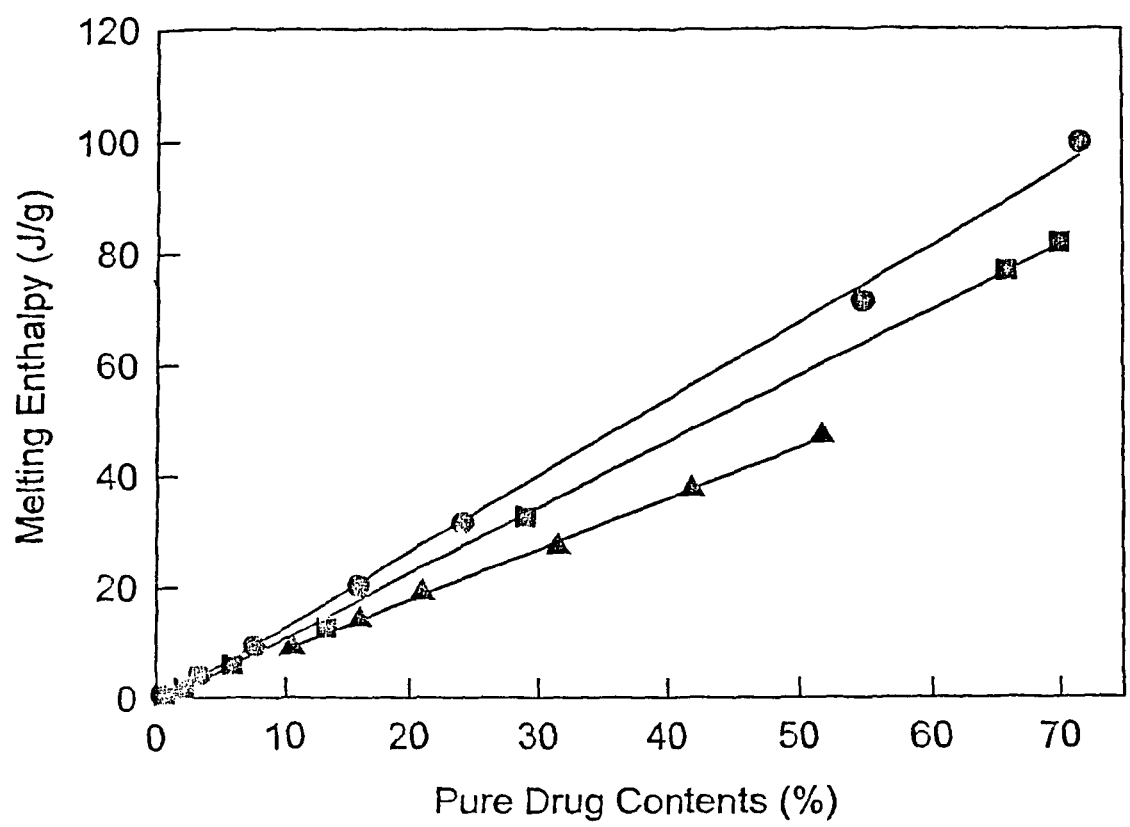
FIG. 1: calibration lines for the ibuprofen β-cyclodextrine, ibuprofen Crosspovidone and Nifedipine Crosspovidone systems.
●: Ibuprofen/beta-Cyclodextrine
■: Ibuprofen/Crosspovidone
▲: Nifedipine/Crosspovidone

A first subject of the invention is constituted by new composites containing a drug dispersed in an organic carrier, in which the drug is:

present in amorphous form in quantities greater than or equal to 50% by weight with respect to the total of the drug present in the composite, and massively dispersed ("in-bulk") within the particles of the above mentioned carrier.

By "drug in amorphous form" is intended the drug when present in the form of molecular clusters, the structural organisation of which is not discernable with X-ray diffraction techniques (PXRD) or by differential scanning calorimetry (DSC). Preferred composites are these which contain at least 75%, or more preferably at least 85% of the drug in amorphous form; composites in which the drug is present at 100% in amorphous form have been obtained with the present invention, and are described in the experimental section.

For "massively dispersed (or in-bulk)" is intended the fact that the drug is deposited not only on the surfaces of the carrier particles, but also inside them: in the present invention the drug is made to diffuse inside carrier particles and stabilised "in situ".

The organic carrier is selected from a cross-linked polymer, a complexing agent or mixtures thereof. The cross-linked polymer is typically water-insoluble, whereas the complexing agent is typically water-soluble; the terms "soluble/insoluble" are meant with respect to water at room temperature (20° C.); the term "cross-linked" refers to the existence of natural or synthetically induced inter-polymer bonds; a preferred example of an insoluble cross-linked polymer is cross-linked polyvinylpyrrolidone, commercially known as crosspovidone; other examples of polymers of this class are cross-linked sodium-carboxymethylcellulose, cross-linked starch, cross-linked dextran, cross-linked polystyrene, cross-linked beta-cyclodextrine.

Preferred members of the class of water-soluble complexing agents are cyclodextrines (such as: alpha-, beta-, gamma-cyclodextrine and derivatives thereof, maltodextrine. The complexing agents may contain water molecules of hydration.

The organic carriers used in the present invention are preferably characterised by non high surface area, for example, between 0.05 and 20 $m^2/g$; for example the CL-PVP and cyclodextrine commercially available meet these requirements perfectly, with an average surface area of 0.5-2 $m^2/g$.

The present invention also comprises the use of mixtures of two or more organic carriers: for example the mixture of an water-insoluble cross-linked polymer with a water-soluble complexing agent.

Any active ingredient of pharmaceutical interest (also including mixtures of two or more of them) can be present in the composites claimed by the present invention; drugs sparingly soluble in water are preferred, also known as belonging to the class II of the biopharmaceutical system of classification (cf. *Guidance for Industry: Immediate Release Solid Oral Dosage Forms*, Ed. Centre for Drug Evaluation and Research, FDA, 1997): examples of such compounds are nimesulide, ibuprofen, nifedipine, grisofulvine, piroxicam, progesterone, indomethacine, lorazepam, etc. As shown in the experimental section, it has been possible to obtain high to complete amorphisation of these products (originally present in the crystalline state with low solubility) and their dispersion in-bulk within the carrier.

In the composites according to the invention, the drug and the carrier are present in weight ratios preferably comprised of between 1:0.5 and 1:20, more preferably between 1:1 and 1:10.

The preparation process of the composites constitutes a second subject of the invention. The process comprises mixing the original drug (i.e. the drug in microcrystalline structure to be made amorphous and dispersed within the carrier) with the above mentioned organic carrier, followed by treatment with an oscillating electromagnetic field, at a frequency belonging to the microwave region, with the following particulars:

(i) the application of the oscillating electromagnetic field is carried out on the previously wetted drug-carrier mixture, or (ii) the application of the oscillating electromagnetic field is carried out on the drug-carrier mixture placed in a container constituted of a dielectric material having coupling capacity with microwaves. In both cases a specific heating cycle is applied, as detailed below.

In the first variant (i), the drug-carrier mixture is wetted with an appropriate amount of solvent, until forming a sufficiently dampened mass; the solvent, generally water, is added using known techniques, for example by nebulisation of the solvent through the mixture kept stirring, or simply pouring onto the mixture and mixing it. The solvent is added in an amount comprised of between 0.1 ml/g and 5 ml/g with respect to the dry drug-carrier mixture. The mixture, thus pre-wetted, placed in a reactor (for example a Pyrex glass container), is introduced into the oven and then treated with microwaves at pressure preferably comprised of between 1 and 20 bar.

In variant (ii), the drug-carrier mixture is placed in a sample holder (reactor) made entirely or partially (for example of at least 10%) of a dielectric material coupling with microwaves, and thus introduced into the microwave applicator. For "coupling capacity by microwaves" is intended the fact that the material in question, when exposed to microwaves, increases the temperature in proportion to the power applied; a preferred example of a material having this property is polytetrafluoroethylene loaded with graphite.

Using reactors containing the above mentioned coupling materials, the amorphisation proceeds easily at atmospheric pressure, without the need to operate at high pressure, and without the need to add water or other humectants; that does not preclude however the possibility of adding water and/or operating under pressure, whenever desired.

In both variants (i) and (ii), the application of the oscillating electromagnetic field is carried out with microwaves having power comprised of between 100 W and 5000 W, for an overall time up to 120 minutes. The oscillating electromagnetic field can indifferently be focussed or non-focussed. The frequency range of the microwaves applied is generally comprised of between 400 MHz and 25000 MHz. The application of the microwaves can take place under conditions of constant or variable power.

The microwave treatment cycle is fundamental according to the present invention. In fact it is required that the microwave power be tuned in such a way that the sample (i.e. the drug-carrier mixture being treated) reaches a temperature value (T°) higher than the melting temperature of the drug contained in the mixture. The temperature T° must then be maintained steady for at least 5 minutes.

There is no specific limit as to how high the temperature T° must be with respect to the drug melting temperature: however it will be preferred to remain rather close to the melting temperature: as a non-limitative indication, T° can be from 1 to 20 degrees C° higher than the drug melting temperature.

By "drug melting temperature" it is meant the temperature corresponding to the peak of the endotherm, as measured by differential scansion calorimetry (DSC), performed at a scanning rate equal to the one set for the dielectric treatment with microwaves.

The microwave treatment can be effected by temporarily setting a specific power level (e.g. 500 W), until the sample reaches the target temperature T°; the latter can be freely chosen by the operator, provided that it is higher than the melting temperature of the drug present in the mixture; once temperature T° is reached, the treatment is prolonged, tuning (modulating) the microwave power so as to maintain the temperature of the sample steady at the temperature T°, for at least 5 minutes.

Alternatively, it is possible to perform a fist step wherein the sample temperature is gradually incremented (for e.g. 10-25 min.), until it reaches the target value T°; subsequently, the treatment is prolonged, tuning (modulating) the microwave power so as to maintain the temperature of the sample steady at the temperature T° for at least 5 minutes.

Figure 4:
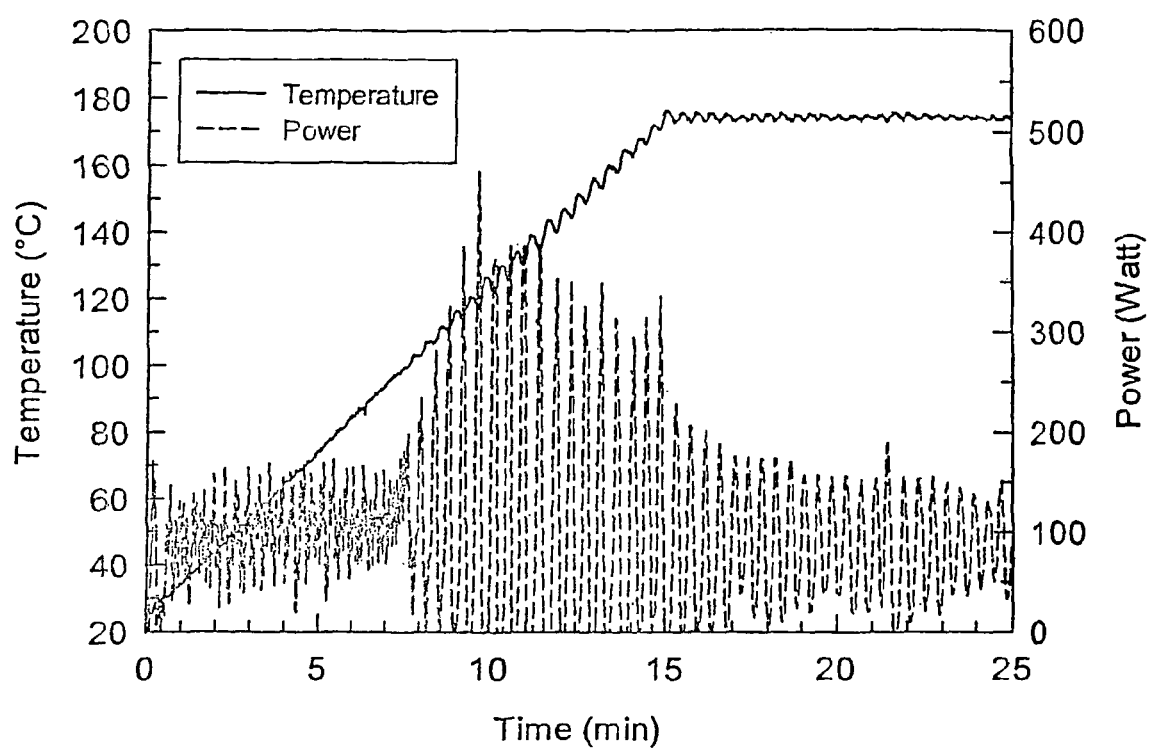
FIG. 4: heating cycle applied in the production of composite PVP/Nif02 (example 1, table 5)

An example of this procedure is illustrated graphically in FIG. 4, showing the temperature recording for the sample PVP/Nif02, prepared and tested by the Applicant (cf. experimental section, example 1, table 5).

In all circumstances the process is always performed at priority of sample temperature, i.e. not of supplied fixed power: the latter is modulated in order to reach and maintain for at least 5 minutes the pre-set temperature T° in the drug-carrier mixture.

In this respect it is important to remark that a melting substance absorbs energy in irregular way, depending on the relative amount of phases (solid, liquid) it goes through during melting. Therefore a steady administration of electromagnetic energy (microwaves power) during the melting process does not produce a parallel steady temperature in the sample; on the contrary, the thus treated sample inevitably shifts in temperature. In order to maintain the sample at a steady temperature, it is necessary to modulate the microwave power, thus compensating continuously for the variable degree of energy absorption of the sample, which takes place during the fusion process. Such compensations are obtainable by available means of electronic systems capable to detect any changes in the sample temperature and to modify immediately, in excess or defect, the microwave power so as to maintain the sample temperature steady at the pre-set T° value.

The equipment used for the application of the microwaves can be any microwave applicator which operates within the above described intervals and is equipped with suitable means to set the microwave power in function of the sample temperature. Such applicators are known per se and already used in the pharmaceutical field for various applications, for example to evaporate solvents. They are generally made up of a microwave generator, a wave guide and an application chamber; the generator is a "magnetron" electronic tube; the wave guide is a corridor, the walls of which are metallic, through a multiple reflection mechanism, they transmit the wave towards the application chamber in which the material is exposed to the microwaves. The applicators are conveniently fitted with power distribution management and control systems, for the sample temperature and the pressure to which the sample is exposed. Specific examples of the distributors used in the present invention are the Prolabo "Synthewave 402" (monomode applicator for focussed microwaves, freq. 2.45 GHz, max. power. 300 W), or the Mileston "Microsynth" (multimode applicator non-focussed microwaves, with pre-mixing chamber and pyramidal diffuser, maximum power 1000 W).

With respect to what allowed by the known art surface amorphisation, amorphisation in-bulk obtained by the present invention allows great exploitation of the entire volume of the available carrier for the incorporation of the drug in amorphous form: it therefore becomes possible to incorporate into the carrier, significantly greater quantities of amorphous drug with respect to that previously possible. Analogously, with equal amorphous drug content, it is possible to reduce the amount of carrier, thus realising lower volume pharmaceutical formulations (e.g. smaller pills), with important advantages both for the saving of excipient, the economy of the process and packaging, and for the ease of administration and acceptability on the part of the patient.

The composites (stabilised solid dispersions) obtained according to the present invention can be used directly as pharmaceutical compositions and as such administered to patients, or can be added to with excipients and treated according to conventional pharmaceutical techniques with the aim of obtaining pharmaceutical forms suited to different administration needs. For example the composite can be integrated with disintegrants, glidants, lubricants, preservatives, sweeteners, other active ingredients, etc. The preparation procedures of pharmaceutical compositions are known per se and comprise for example granulation, compression, film-coating, encapsulation, micro-encapsulation, etc.; the pharmaceutical forms in which the composite can be formulated include granulates for extemporaneous dissolution, pills, mini-pills, capsules, microcapsules, etc.

The present invention will now be described through the following example applications, which do not have limiting function.

Experimental Section

Materials and Methods

1. Active Ingredients
   The materials subjected to treatment with microwaves are:
   Ibuprofen, Nimesulide and Nifedipine, representatives of sparingly hydrosoluble drugs, belonging to the biopharmaceutical class II.
   The thermal characteristics of Ibuprofen are the following:
   Melting temperature $T_m$=75.6° C.,
   Melting enthalpy $\Delta H_m$=126.6 J/g.
   The thermal characteristics of Nimesulide are the following:
   Melting temperature $T_m$=148.9° C.
   Melting enthalpy $\Delta H_m$=111.1 J/g).
   The thermal characteristics of Nifedipine are the following:
   Melting temperature $T_m$=172.7° C.
   Melting enthalpy $\Delta H_m$=101.4 J/g).
2. Organic Carriers
   Crosspovidone, as an insoluble amphiphilic cross-linked polymer.

β-cyclodextrine, as a carrier belonging to the class of the hydrosoluble complexing agents.

3. Microwave Applicators

The "Synthewave 402" monomode applicator from Prolabo, operating at a frequency of 2.45 GHz and with a maximum deliverable power of 300 Watts. With this type of applicator the field results as being focused in a restricted spatial volume containing the sample for treatment.

The "Microsynth" multimode applicator from Milestone fitted with a premixing chamber with a pyramidal microwave diffuser to obtain optimal uniformity of the field. The applicator works with two continuous generation magnetrons (non pulsed) and distributes a maximum power of 1000 Watts.

Both applicators are equipped with control systems for the delivered power, the developed pressure (up to 20 bar) and the temperature of the sample. The control and monitoring system for the monitoring of the sample temperature is constituted of two types of sensors: one fibre-optic and the other infrared (pyrometer).

4. Characterisation of the Physical State of the Drug in the Composites (Degree of Dispersion and Degree of Amorphisation)

Figure 5:
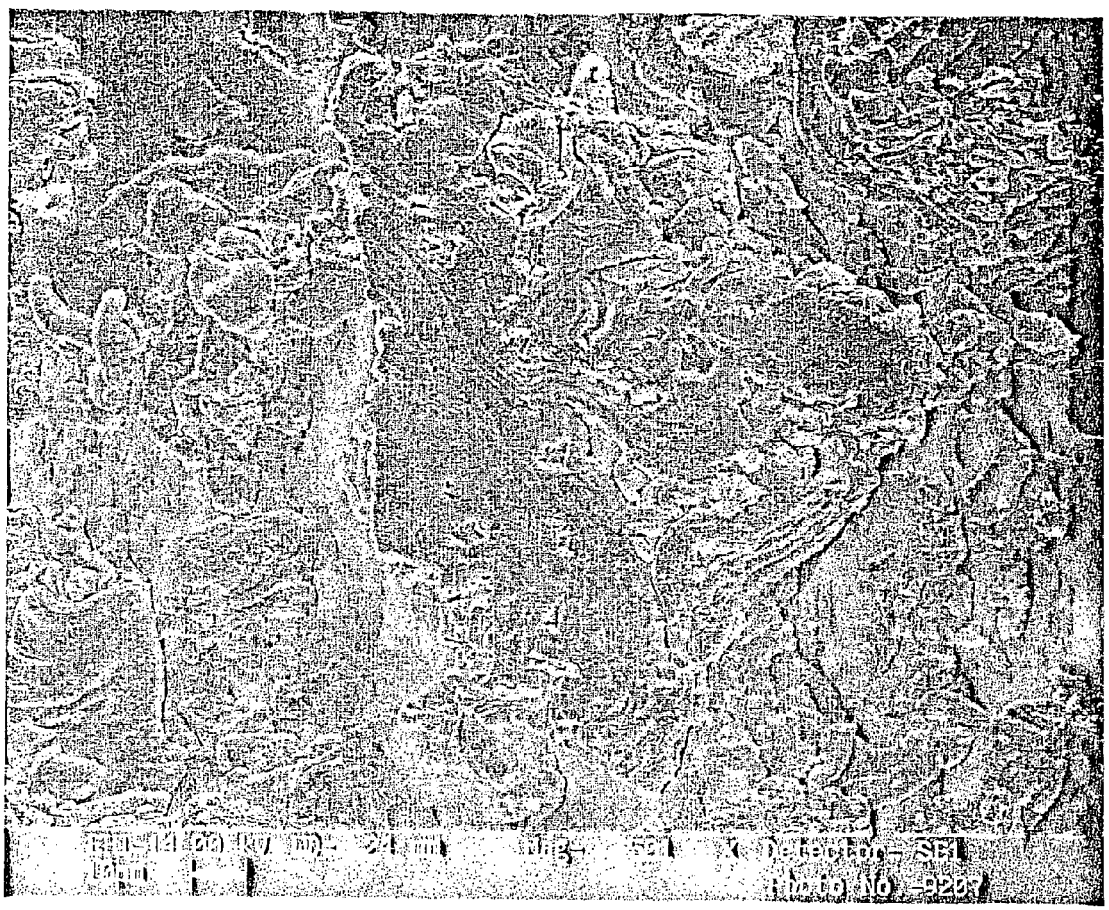
FIG. 5: section of a particle of composite PVP/Nim02 (example 1, table 4) observed by scansion electronic microscope.

The degree of dispersion of the drug in the carrier has been evaluated by SEM-EDS (scanning electronic microscopy and energy dispersion spectroscopy). This technique allows to map, quali-quantitatively, the spatial distribution of single atoms onto the microscope image of the carrier particles; this is done via the acquisition of the X-ray emission spectrum caused by the interaction between the primary electrons and the material. Since it was desired to obtain a quantitative information on the dispersion of amorphous drug within the particles of composite, it was necessary to prepare a section of said particles by a microtome, and to fix it within a epoxy resin matrix. In FIG. 5 a SEM image of a section of a crospovidone particle is shown.

The percentage of crystalline residue has been calculated using the following relationship:

$$\%C = \frac{(\Delta H_a * 100)}{slope * T}$$

where % C is the residual percentage crystallinity of the drug, $\Delta H_a$ is the apparent specific enthalpy of fusion, determined by DSC, T is the percentage drug content in the system and the constant "slope" represents the angular coefficient of the calibration line obtained by measuring the enthalpy of fusion in drug-carrier physical mixtures pre-constituted with known drug content (as an example see FIG. 1). The % of drug in the amorphous state (% A) is:

%$A$=(100%−%$C$)

In the following experiments (examples 1-3) a series of drug-carrier mixtures has been subjected to the amorphisation process according to the present invention.

Example 1

Physically homogeneous mixtures of Ibuprofen with β-cyclodextrine hydrate and Ibuprofen with Crosspovidone in weight ratios of 1 to 9 have been prepared; approx. 5 grams of the mixture, for each test, have been inserted into a Pyrex glass reactor (a material non-coupling with the microwaves) inside the applicator of the monomode oven. To each mixture, appropriately kept stirring by a mechanical stirrer in Pyrex glass (operating at 3 revolutions per minute), has been added an amount of purified water equal to 1 ml per gram of β-cyclodextrine. (samples Beta/Ibu13, Beta/Ibu14, Beta/Nim01, Beta/Nim03) or 2 ml per gram of Crosspovidone (samples PVP/Ibu01, PVP/Ibu02, PVP/Nim01), or 3 ml per gram of Crosspovidone (samples PVP/Nim02, PVP/Nim03, PVP/Nim04, PVP/Nif02). The wet mixtures have then been subjected to treatment with microwaves at programmed temperature and at atmospheric pressure under the operative conditions reported in tables 1 and 2.

For irradiation, a monomode "Synthewave 402" applicator from Prolabo has been used, operating at a frequency of 2.45 GHz and with a maximum deliverable power of 300 Watts.

The results obtained are illustrated in the two following tables.

TABLE 1 operative conditions of the process and values of residual crystallinity of the Ibuprofen β-cyclodextrine composites obtained with the monomode applicator.

| Samples | Drug content (%) | Temperature program | Total time (minutes) | Residual crystallinity (*) (%) |
|---|---|---|---|---|
| Beta/Ibu13 | 10 | From 25° C. to 90° C. in 15' & 10' at 90° C. | 25 | 22.7 |
| Beta/Ibu14 | 10 | From 25° C. to 90° C. in 15' & 20' at 90° C. | 35 | 21.6 |

(*) % of crystallinity with respect to the crystallinity of the original drug (=100%).

TABLE 2 operative conditions of the process and residual crystallinity values of the Ibuprofen Crosspovidone composites obtained with the monomode applicator.

| Samples | Drug content (%) | Temperature program | Total time (minutes) | Residual crystallinity (%) |
|---|---|---|---|---|
| PVP/Ibu01 | 10 | From 25° C. to 90° C. in 15' & 10' at 90° C. | 25 | 0.0 |
| PVP/Ibu02 | 10 | From 25° C. to 80° C. in 15' & 15' at 80° C. | 30 | 0.0 |

The same approach has been used with a drug having different thermal characteristics to the previous (Nimesulide, $T_m$=148.9° C., $\Delta H_m$=111.1 J/g). The method variations and the crystallinity data are reported in tables 3 and 4.

TABLE 3 operative conditions of the process and residual crystallinity values of the Nimesulide β-cyclodextrine composites obtained with a monomode applicator.

| Samples | Drug content (%) | Temperature program | Total time (minutes) | Residual crystallinity (%) |
|---|---|---|---|---|
| Beta/Nim01 | 10 | From 25° C. to 160° C. in 20' & 10' at 160° C. | 30 | 32.0 |
| Beta/Nim03 | 10 | From 25° C. to 160° C. in 20' & 20' at 160° C. | 40 | 40.7 |

TABLE 4 operative conditions of the process and residual crystallinity values of the Nimesulide Crosspovidone composites obtained with a monomode applicator.

| Samples | Drug content (%) | Temperature program | Total time (minutes) | Residual crystallinity (%) |
|---|---|---|---|---|
| PVP/Nim01 | 10 | From 25° C. to 150° C. in 20' & 10' at 150° C. | 30 | 45.4 |
| PVP/Nim02 | 10 | From 25° C. to 150° C. in 20' & 10' at 150° C. | 30 | 39.4 |
| PVP/Nim03 | 16.7 | From 25° C. to 150° C. in 15' & 15' at 150° C. | 30 | 38.0 |
| PVP/Nim04 | 16.7 | From 25° C. to 150° C. in 15' & 30' at 150° C. | 45 | 36.6 |

The same process has been used with Nifedipine, using the "Mictrosynth" multimode applicator. The process parameters and the crystallinity characteristics are reported in table 5.

TABLE 5 operative conditions of the process and residual crystallinity values of the Nifedipine Crosspovidone composite obtained with the multimode applicator.

| Samples | Drug content (%) | Temperature program | Total time (minutes) | Residual crystallinity (%) |
|---|---|---|---|---|
| PVP/Nif02 | 16.7 | From 25° C. to 175° C. in 15' & 10' at 175° C. | 35 | 0.0 |

The graphic registration of the sample temperature in this test is shown in FIG. 4. The low or zero residual crystallinity percentages observed in the examples shown demonstrate the achievement of high grades of amorphisation. In particular, in the case of ibuprofen and nifedipine, composites characterised by complete amorphisation of the drug (0% residual crystallinity) are obtained.

Assessment of Drug Dispersion within the Carrier Matrix

The in-bulk dispersion of the active principle was confirmed by SEM-EDS observations, as follows.

Figure 6:
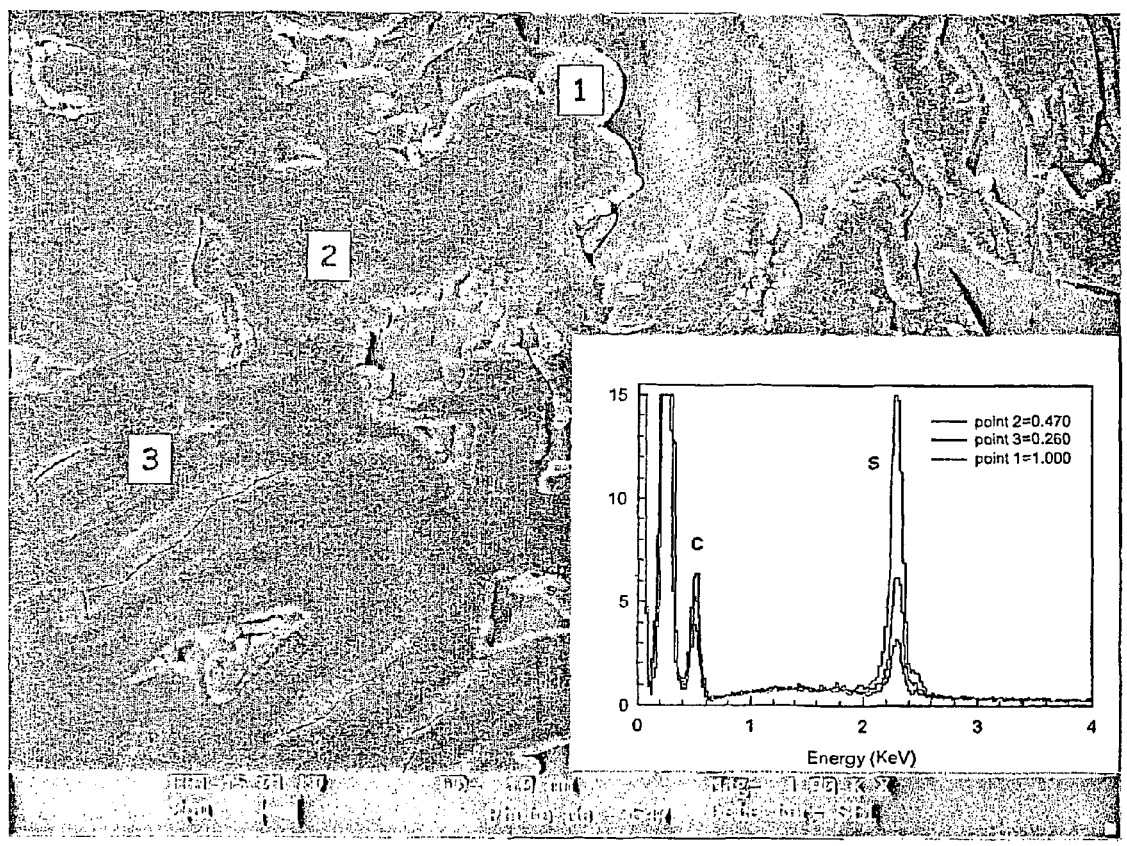
FIG. 6: magnified image of the particle of FIG. 5, with analysis of drug concentration in three different points of the particle section.

The presence of sulphur was quantitatively assessed in an area of the section of the particle of PVP/Nim 02m, shown in FIG. 6. Sulphur, which is part of the drug molecule (nimesulide), and not of the carrier (crospovidone), was searched in three points located at growing distance from the surface of the particle, marked with numbers 1, 2, 3 in FIG. 6. As evident from the X ray spectra shown in the box of FIG. 6, the sulphur atom was detected in high amounts in all points, thus proving the presence of the drug also inside the polymeric carrier. The inner part of the section shows the homogeneity typical of a solid dispersion (amorphous drug dispersed within the amorphous polymer matrix).

This demonstrates that a massive dispersion (in-bulk) of the amorphised drug is achieved, i.e. not only on the surfaces of the carrier particles, but deep within them.

A further demonstration of the in-bulk dispersion of the drug is obtained via the following calculation:
considering that the drug/polymer weight ratio used in the preceding experiments is equal to 1:5, (PVP/Nim 04) the mass balance of the composite is:

$$M_T = M_{DC} + M_{DA} + M_C$$

wherein: $M_{DC}$ represents the mass of the crystalline drug in the composite, $M_{DA}$ the mass of the amorphous drug, $M_C$ the mass of the carrier and $M_T$ the total mass.

For the examples reported, it will be:

$$M_{DC} = 206.4 \text{ mg} * 0.366 = 75.5,$$

$$M_{DA} = 206.4 \text{ mg} - 75.5 = 130.9,$$

$$M_C = 1028.9 \text{ mg and } M_T = 1235.4 \text{ mg}.$$

Since the PVP-CL used has a specific surface area of 4.5 m²/g (values determined experimentally by adsorption isotherms method B.E.T.) the weight fraction contained in the composite has a total surface development equal to 4.5*0.833=3.75 m²/g.

Reasonably, the drug molecules which can be stabilised in amorphous form on the surfaces of carriers constitute a molecular monolayer interacting with the surfaces themselves.

The drug molecule can interact with the molecules of polyvinylpyrrolidone, which are present on the surfaces of the carrier, with interactions which are either hydrophobic or hydrophilic in nature (remembering the amphiphilic nature of the polymer used); estimating the molecular surface development of the nimesulide, characterised by these two interactions, one can calculate the area occupied by a single molecule interacting with the surface.

Using the three dimensional molecular structure of nimesulide, minimised with both molecular mechanical (MMFF force field) and semi-empirical (AM1) algorithms with the software "Spartan 02", the two molecular descriptors involved can be calculated (molecular surface area with hydrophobic characteristics and molecular surface area with hydrophilic characteristics). The measurement of these descriptors has been performed with the molecular prediction software "QikProp" and has given the following values:
hydrophobic molecular surface area=0.9 nm²
hydrophilic molecular surface area=1.75 nm²

Considering the two contributions, the surface covered by a single molecule of nimesulide is equal to 2.65 nm².

The quantity of molecules necessary to constitute an amorphous monolayer on the surface of the carrier will be given by 3.75 m²*g⁻¹/2.65*10⁻¹⁸ m²=140.7*10¹⁶ molecules, i.e. 0.721 mg of nimesulide. Rewriting the equation to balance with these values for $M_{DA}$, one obtains a value of $M_{DC}$=205.7 mg equal to 99.6% of crystallinity.

Hence, one can conclude that the excess of amorphous drug involved in preparation PVPNIM02 is found dispersed to a large measure inside (in-bulk) the carrier particles.

Example 2

Homogeneous physical mixtures of Nimesulide with Crosspovidone and β-cyclodextrine have been prepared in weight ratios 1 to 2 and 1 to 5, physical mixtures of Nifedipine with Crosspovidone 1 to 5 (w/w); approx. 5 grams of the mixture, for each test, have been inserted into a PTFE container loaded with graphite and then placed inside the application chamber of a multimode "Microsynth" oven (Mileston). In addition, a 1 to 9 Ibuprofen β-cyclodextrine mixture has been prepared and treated in the same oven, setting the power of the oven to a fixed and constant value, for the time of treatment, equal to 600 Watts. Water has not been added and the reaction environment has been maintained at atmospheric pressure (1 atm).

The process conditions and the physical characteristics of the composites obtained are reported in table 6.

TABLE 6 operative conditions of the process and residual crystallinity values of the Nimesulide β-cyclodextrine, Ibuprofen β-cyclodextrine, Nimesulide Crosspovidone and Nifedipine Crosspovidone composites obtained with the multimode applicator.

| Samples | (w/w)[a] | Temperature program | Total time (minutes) | Residual crystallinity (%) |
|---|---|---|---|---|
| PVP/Nim05 | 1 to 2 | From 25° C. to 150° C. in 10' & 10' at 150° C. | 30 | 27.3 |
| PVP/Nif04 | 1 to 5 | From 25° C. to 175° C. in 15' & 10' at 175° C. | 25 | 1.0 |
| BetaIbu15 | 1 to 9 | 600 W up to 80° C. & 5' at 80° C. | 5 | 23.8 |
| BetaIbu16 | 1 to 9 | 600 W up to 80° C. & 3' at 80° C. | 3 | 38.4 |

[a] = weight ratio between drug and carrier

The residual crystallinity values indicate also in this case a high degree of amorphisation of the drug. The distribution in-bulk of the drug has been confirmed with the above described methods.

Example 3

A mixture of Nimesulide/Crosspovidone in a weight ratio of 1 to 5 has been prepared; approx. 6 grams of mixture have been inserted into the reactor of the multimode applicator. To the mixture have been added approx. 10 ml of purified water. The mixture, thus wetted, has been subjected to treatment with microwaves at temperature program temperature and at increasing pressure according to the phase diagram of water (at constant volume): from 1 bar (at T=25° C.) up to 5 bar (at T=155° C.).

The process conditions and the residual crystallinity obtained are reported in the following table 7:

| Samples | Drug content (%) | Temperature program | Total time (minutes) | Residual crystallinity (%) |
|---|---|---|---|---|
| PVP/Nim07 | 16.7 | From 25° C. to 155° C. in 10' & 10' at 155° C. and P = 5 bar | 25 | 45.0 |

Example 4

Reference

To verify the criticality of the treatment used in the present invention, a Nimesulide-Crosspovidone physical mixture has been prepared in the weight ratio 1 to 5; approx. 2 grams of mixture have been introduced into a general reactor (in Pyrex glass) inside a monomode applicator. Differently from that requested in the present invention, the reactor used is not based on dielectric materials coupling with the microwaves. The mixtures thus obtained have been successively subjected to treatment with microwaves at temperature program temperature and at reduced pressure ($0.1*10^5$ Pa) under the operative conditions reported in the table 8.

TABLE 8 operative conditions and residual crystallinity values of Nimesulide-Crosspovidone composites.

| Samples | Drug content (%) | Temperature program | Total time (minutes) | Residual crystallinity (%) |
|---|---|---|---|---|
| PVP/Nim06 | 16.7 | From 25° C. to 150° C. in 10' & 15' at 150° C. | 25 | 96.0 |
| PVP/Nif01 | 16.7 | From 25° C. to 170° C. in 10' & 15' at 170° C. | 25 | 97.5 |

Figure 2:
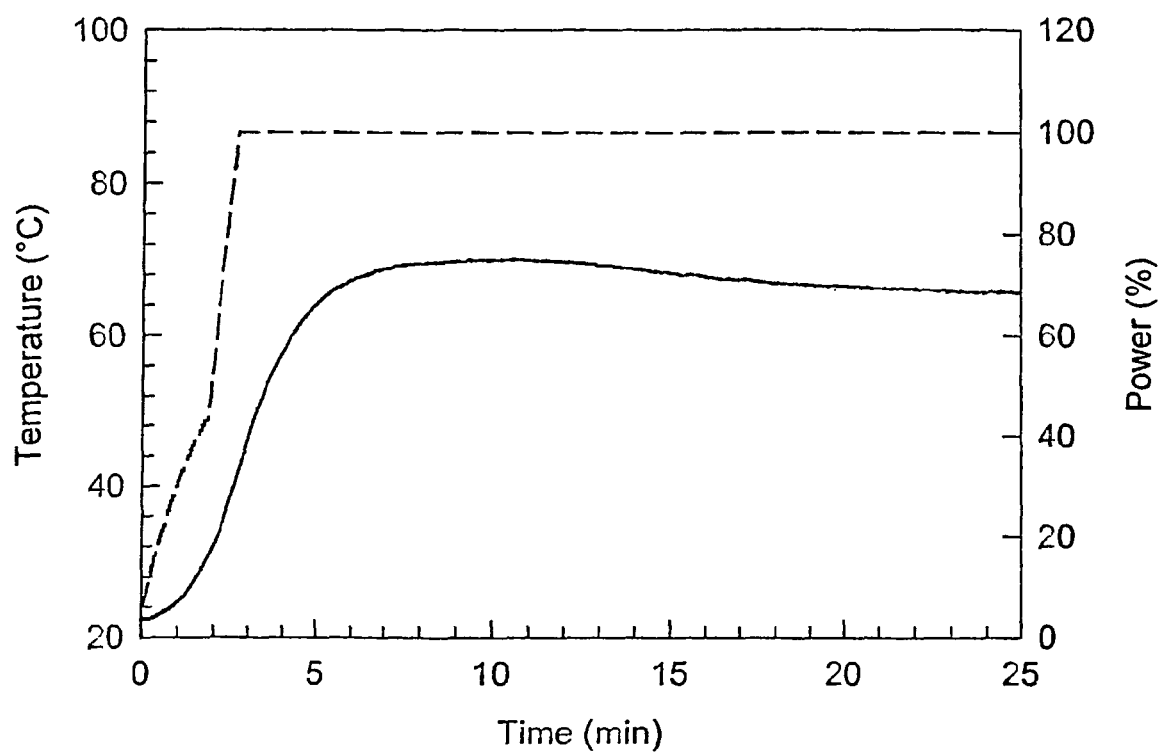
FIG. 2: power ( - - - ) and temperature (—) profiles obtained during the treatment of the sample PVP/Nif01. (example 4, table 8).
Figure 3:
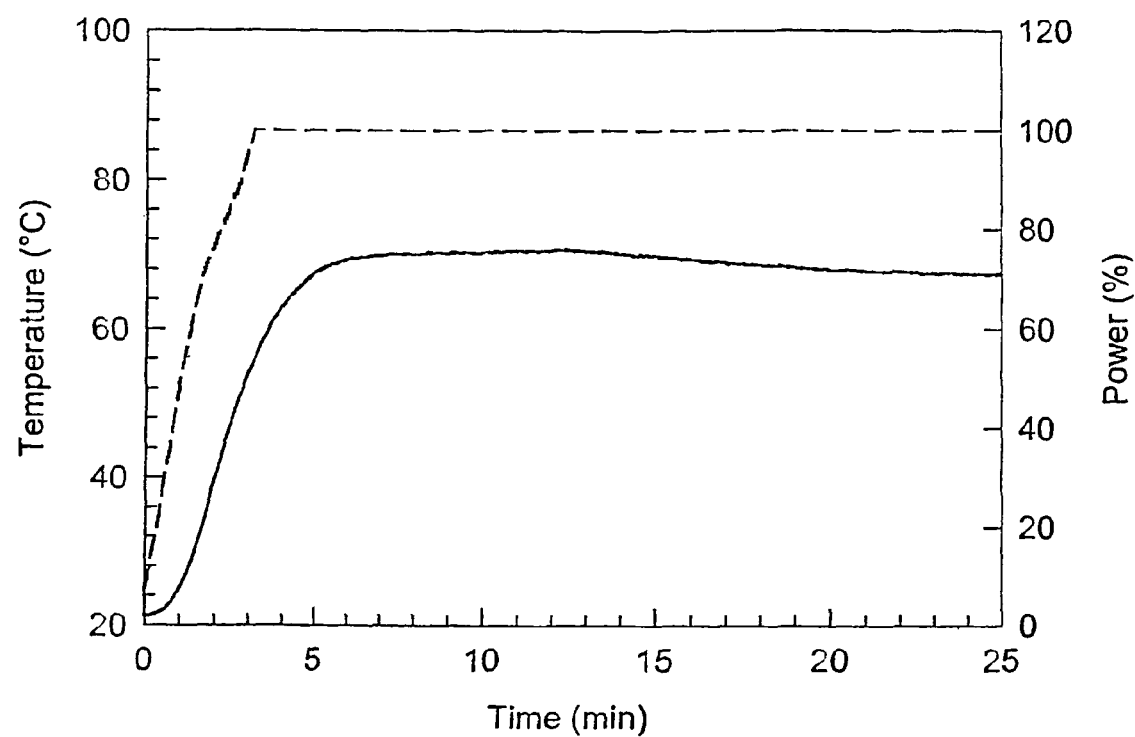
FIG. 3: power (- - -) and temperature (—) profiles obtained during the treatment of the sample PVP/Nim06 (example 4, table 8).

As is clear from the data of the percent residual crystallinity (96-97%), the treatment has not been able to obtain any amorphisation: the drug maintains its crystallinity substantially unaltered. These data demonstrate that, when operating in dry conditions, in the absence of reactors coupling with the microwaves, it is not possible to obtain any dispersion of amorphised drug. In FIGS. 2 and 3 are shown the temperature profiles of the two reference samples during the treatment cycle: as is clear from the figures, both mixtures treated do not have significant temperature increases such as to induce solid-liquid transitions in the crystalline drugs, despite using the maximum power of the applicator used; that further confirms the absence of amorphisation of drug under these experimental conditions.

Example 5

Reference

In this example a drug-carrier mixture was dry-treated with microwaves; differently from the invention, linear polyvinylpyrrolidone was used as a carrier, which is neither a cross-linked polymer, or a complexing agent; the power applied was maintained constant throughout the entire treatment, following the teaching of the prior art, e.g. example 1 of EP 1308156.

Thus 1 g of Nifedipine and 5 g of polyvinylpyrrolidone K30 were put into a teflon reactor and treated with microwaves for 4 minutes at a power of 630 W. The residual crystallinity of the thus treated material, determined by DSC, was 93.2%. Accordingly, less than 7% of the drug was converted into amorphous form.

Example 6

Reference

In this example the sample was wet-treated with microwaves, using nifedipine as a drug and cross-linked polyvinylpyrrolidone as a carrier; differently from the invention, the power applied was maintained constant throughout the entire treatment following the teaching of the prior art, e.g. example 4 of U.S. Pat. No. 6,462,093. Thus, 1.25 g of water were added to a mixture made of 1 g of Nifedipine and 5 g of crospovidone in a teflon reactor and treated with microwaves (2.45 GHz) with a power of 700 W for 20 minutes. After 5 minutes the treatment was suspended because the mixture was completely decomposed leaving only a carbonised residue. The same tests was repeated using only crospovidone without adding water. After about 10 minutes of treatment at 700 W the material was completely carbonised as in the previous test. This phenomenon is presumably due to a "thermal runaway" caused by a sudden increase of the imaginative part of complex permittivity (loss factor) with temperature. Such increase result in a growing dielectric coupling and thus a further increase in the sample temperature (for a review on these phenomena cf. Committee on microwave processing of materials: an emerging industrial technology. Microwave processing of materials, pag. 36, Publication NMAB-473. Washington: National academy Press, 1994).

The invention claimed is:

1. A process for the preparation of a composite containing a drug dispersed in a particulate organic carrier, comprising:
   a) mixing a drug and a particulate organic carrier selected from the group consisting of water-soluble complexing agents, water-insoluble cross-linked polymers, and mixtures thereof; and
   b) applying an oscillating electromagnetic field to the mixture, wherein the oscillating electromagnetic field is microwave irradiation modulated to increase the temperature of the mixture to a temperature greater than the melting temperature of the drug and maintained at the temperature greater than the melting temperature of the drug for at least 5 minutes to provide a composite containing the drug, wherein the drug is dispersed inside of the organic carrier particles as well as on the external surface of the particles, wherein the drug is present in the composite in amorphous form in a quantity greater than or equal to 50% by weight based on the total amount of the drug.

2. The process of claim 1, wherein mixing a drug and a particulate organic carrier further comprises adding a solvent to provide a wet mixture.

3. The process of claim 2, wherein said solvent is water.

4. The process of claim 3, wherein said wet mixture is formed by adding water to the drug and particulate organic carrier in a quantity between 0.1 ml/g and 5 ml/g based on the weight of drug and particulate organic carrier.

5. The process of claim 2, wherein the oscillating electromagnetic field is applied to the mixture at a the pressure between 1 and 20 bar.

6. The process of claim 1, wherein the oscillating electromagnetic field is applied to the mixture in a container comprising a dielectric material having coupling capacity with microwaves.

7. The process of claim 6, wherein said dielectric material is polytetrafluoroethylene loaded with graphite.

8. The process of claim 1, wherein the microwave irradiation is carried out with power in the range between 100 W and 5000 W, for a time up to 120 minutes.

9. The process of claim 1, wherein said cross-linked polymer is selected from the group consisting of cross-linked polyvinylpyrrolidone, cross-linked sodium carboxymethylcellulose, cross-linked starch, cross-linked dextran, cross-linked polystyrene and cross-linked β-cyclodextrin.

10. The process of claim 1, wherein said drug is a drug sparingly soluble in water.

11. The process of claim 1, wherein said water-soluble complexing agents are selected from the group consisting of cyclodextrins, maltodextrins, and mixtures thereof.

* * * * *